United States Patent
Lee et al.

(10) Patent No.: US 9,765,013 B2
(45) Date of Patent: Sep. 19, 2017

(54) METHOD FOR PREPARING AROMATIC CARBONATE

(71) Applicant: SAMSUNG SDI CO., LTD., Yongin-si (KR)

(72) Inventors: Chang Hoon Lee, Uiwang-si (KR); Dong Baek Kim, Uiwang-si (KR); Yeon Ju Lee, Uiwang-si (KR); O Sung Kwon, Uiwang-si (KR); Il Hwan Yang, Uiwang-si (KR)

(73) Assignee: Lotte Advanced Materials Co., Ltd., Yeosu-si (KR)

( * ) Notice: Subject to any disclaimer, the term of this patent is extended or adjusted under 35 U.S.C. 154(b) by 0 days.

(21) Appl. No.: 15/025,379

(22) PCT Filed: Jan. 16, 2014

(86) PCT No.: PCT/KR2014/000450
§ 371 (c)(1),
(2) Date: Mar. 28, 2016

(87) PCT Pub. No.: WO2015/050291
PCT Pub. Date: Apr. 9, 2015

(65) Prior Publication Data
US 2016/0237019 A1    Aug. 18, 2016

(30) Foreign Application Priority Data

Oct. 2, 2013    (KR) .................. 10-2013-0118207

(51) Int. Cl.
*C07C 68/06*    (2006.01)
*C07C 68/04*    (2006.01)

(52) U.S. Cl.
CPC .............. *C07C 68/06* (2013.01); *C07C 68/04* (2013.01); *Y02P 20/142* (2015.11)

(58) Field of Classification Search
CPC .................... C07C 68/06; C07C 68/04
See application file for complete search history.

(56) References Cited

U.S. PATENT DOCUMENTS

| | | | |
|---|---|---|---|
| 7,417,161 B2 * | 8/2008 | Woo | ........................ C07C 68/06 558/270 |
| 7,435,842 B2 | 10/2008 | Miyake et al. | |
| 7,446,218 B2 | 11/2008 | Miyake et al. | |
| 7,541,482 B2 | 6/2009 | Miyake et al. | |
| 7,629,485 B2 | 12/2009 | Miyake | |
| 7,652,122 B2 | 1/2010 | Miyake et al. | |
| 8,008,518 B2 | 8/2011 | Shinohata et al. | |
| 8,168,812 B2 | 5/2012 | Shinohata et al. | |
| 8,580,996 B2 * | 11/2013 | Kim | ........................ C07C 68/06 528/370 |
| 8,759,561 B2 * | 6/2014 | Kim | ........................ B01J 31/122 556/83 |

FOREIGN PATENT DOCUMENTS

| | | |
|---|---|---|
| CN | 1839112 A | 9/2006 |
| CN | 101522697 A | 9/2009 |
| JP | 2001-396537 A | 7/2003 |
| JP | 2001-396545 A | 7/2003 |
| JP | 2006-095140 A | 10/2007 |
| JP | 2003-556375 | 7/2008 |
| JP | 2005-511122 B2 | 8/2008 |
| JP | 2006-548937 B2 | 2/2009 |
| JP | 2006-513613 B2 | 4/2009 |
| JP | 2010-523783 B2 | 11/2012 |
| KR | 10-2004-0061017 A | 7/2004 |
| KR | 10-2005-0030631 A | 3/2005 |
| KR | 10-2006-0027816 A | 3/2006 |
| KR | 10-2009-0033266 A | 4/2009 |
| WO | 2015/050291 A1 | 4/2015 |

OTHER PUBLICATIONS

International Search Report in counterpart International Application No. PCT/KR2014/000450 dated Jul. 29, 2014, pp. 1-6.
Office Action in counterpart Chinese Application No. 201480055002.9 dated Aug. 30, 2016, pp. 1-6.

* cited by examiner

*Primary Examiner* — Golam M M Shameem
(74) *Attorney, Agent, or Firm* — Addition, Higgins & Pendleton, P.A.

(57) ABSTRACT

A method for preparing an aromatic carbonate, of the present invention, comprises the steps of: (A) preparing a reaction mixture containing an aliphatic carbonate by reacting an organometallic compound and carbon dioxide; and (B) preparing an aromatic carbonate by reacting the reaction mixture and an aromatic alcohol. The method for preparing an aromatic carbonate allows an aromatic carbonate to be economically prepared in a high yield by using carbon dioxide as a carbonyl supply source.

6 Claims, No Drawings

METHOD FOR PREPARING AROMATIC CARBONATE

CROSS-REFERENCE TO RELATED APPLICATIONS

This application claims priority to and the benefit of International Application No. PCT/KR2014/000450, filed Jan. 16, 2014, which published as WO 2015/050291 on Apr. 9, 2015, and Korean Patent Application No. 10-2013-0118207, filed in the Korean Intellectual Property Office on Oct. 2, 2013, the entire disclosure of each of which is incorporated herein by reference.

TECHNICAL FIELD

The present invention relates to a method for preparing an aromatic carbonate. More particularly, the present invention relates to a method for preparing an aromatic carbonate, which can economically prepare an aromatic carbonate in high yield using carbon dioxide as a carbonyl source.

BACKGROUND ART

An aromatic carbonate is an eco-friendly carbonyl source capable of replacing phosgene, which is a very toxic compound. An aromatic carbonate can be obtained through reaction of an aromatic alcohol compound with carbon monoxide, carbon dioxide, urea, and the like. However, this method has problems of generation of by-products during reaction, inclusion of impurities in a product, use of an expensive catalyst, complex processes, and the like.

To overcome these problems, a method for preparing an aromatic carbonate through transesterification between an aliphatic carbonate and an aromatic alcohol has been developed. Here, compounds such as PbO, TiX$_4$ (X=an alkoxy group, an aryloxy group, or a halogen group), and SnR$_2$(X)$_2$ (R=an alkyl group, an alkoxy group, an aryloxy group, or a halogen group) are considered to be a desirable catalyst. Since these catalysts generate water, an alcohol, a halogen compound, and the like through reaction with an aromatic alcohol, these catalysts are converted into a metal phenoxide through pretreatment with an aromatic alcohol in preparation of an aromatic carbonate, instead of being directly used. However, this method has problems of difficulty of transportation due to low solubility of a metal phenoxide, cumbersome pretreatment, and catalyst preparation costs.

There has also been developed a method wherein carbon dioxide is reacted with ethylene oxide and the like to prepare a cyclic carbonate, followed by reacting the carbonate with an aliphatic alcohol, thereby producing an aliphatic carbonate to be used in preparation of an aromatic carbonate. This method has advantages in that harmless carbon dioxide is used as a carbonyl source, and corrosive materials such as hydrochloric acid are hardly used or generated. However, this method can cause side reactions such as generation of ethylene glycol, and has a limitation relating to plant location due to difficulty in safe transport of ethylene oxide or ethylene, which is a source of ethylene oxide.

Recently, a method for preparing an aliphatic carbonate by reacting carbon dioxide, as a carbonyl source, with an organometallic compound has been studied. It has also been found that, after separation of an aliphatic carbonate from a mixture produced by the method, the organometallic compound can be reproduced by reaction of a residual liquid with an alcohol. In other words, the used organometallic compound can be recycled to be reused in formation of the aliphatic carbonate. As such an organometallic compound, there are disclosed compounds of formula Sn(R)$_2$(OR')$_2$ (R and R' being two different alkyl groups), which includes tin as a center metal and contains two alkyl groups and an alkoxy group (Japanese Patent Application No. 2010-523783 A, No. 2006-548937 A, No. 2006-513613 A, No. 2006-095140 A, No. 2005-511122 A, No. 2003-556375 A, No. 2001-396545 A, No. 2001-396537 A, and the like).

However, these organometallic compounds must be regenerated after reaction in order to be recycled. Therefore, there is a need for a method which can avoid costs for regeneration of an organometallic compound and can economically prepare an aromatic carbonate in high yield using carbon dioxide as a carbonyl source without a need for use of an expensive catalyst, complex processes, and the like.

DISCLOSURE

Technical Problem

It is an object of the present invention to provide a method for preparing an aromatic carbonate, which can economically prepare an aromatic carbonate in high yield using carbon dioxide as a carbonyl source.

The above and other objects of the present invention can be achieved according to embodiments of the present invention.

Technical Solution

An aspect of the present invention relates to a method for preparing an aromatic carbonate. The method includes: (A) preparing a reaction mixture containing an aliphatic carbonate by reacting an organometallic compound with carbon dioxide; and (B) preparing an aromatic carbonate by reacting the reaction mixture with an aromatic alcohol.

In one embodiment, the aliphatic carbonate in the reaction mixture may be reacted with the aromatic alcohol without being separated.

In one embodiment, the organometallic compound may contain a metal-oxygen-carbon bond.

In one embodiment, the organometallic compound may include at least one of an organometallic compound represented by Formula 1 and an organometallic compound represented by Formula 2:

[Formula 1]

wherein M$_a$ is a Group IV or Group XIV element; R$_1$ is a C$_1$ to C$_{12}$ hydrocarbon group; R$_2$ is a linear or branched C$_1$ to C$_{12}$ aliphatic hydrocarbon group or a cyclic C$_5$ to C$_{12}$ aliphatic hydrocarbon group; a is an integer from 0 to 2; b is an integer from 2 to 4; and a+b is 4,

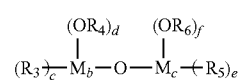
[Formula 2]

wherein M$_b$ and M$_c$ are each independently a Group IV or Group XIV element; R$_3$ and R$_5$ are each independently a C$_1$ to C$_{12}$ hydrocarbon group; R$_4$ and R$_6$ are each independently a linear or branched C$_1$ to C$_{12}$ aliphatic hydrocarbon group or a cyclic $C_5$ to $C_{12}$ aliphatic hydrocarbon group; c and e are each independently an integer from 0 to 2; d and f are each independently an integer from 1 to 3; and c+d and e+f are each independently 3.

In one embodiment, the preparing an aliphatic carbonate (step (A)) may be performed at about 130° C. to about 230° C. at a carbon dioxide pressure of about 10 bar to about 200 bar.

In one embodiment, the preparing an aromatic carbonate (step (B)) may be performed at about 100° C. to about 250° C. at about 1 bar to about 30 bar.

In one embodiment, the preparing an aliphatic carbonate (step (A)) may be performed in the presence of an alcohol containing a linear or branched $C_1$ to $C_{12}$ aliphatic hydrocarbon group or an alcohol containing a cyclic $C_5$ to $C_{12}$ aliphatic hydrocarbon group.

Advantageous Effects

According to the present invention, it is possible to provide a method for preparing an aromatic carbonate, which can economically prepare an aromatic carbonate in high yield using carbon dioxide as a carbonyl source.

BEST MODE

Hereinafter, embodiments of the present invention will be described in detail.

A method for preparing an aromatic carbonate according to the present invention includes: (A) preparing a reaction mixture containing an aliphatic carbonate by reacting an organometallic compound with carbon dioxide; and (B) preparing an aromatic carbonate by reacting the reaction mixture with an aromatic alcohol.

The organometallic compound contains a metal-oxygen-carbon bond and may include an aliphatic alkoxy group-containing organometallic compound used in a typical method for preparing an aliphatic carbonate using carbon dioxide as a carbonyl source.

In one embodiment, the organometallic compound may include at least one of an organometallic compound represented by Formula 1 and an organometallic compound represented by Formula 2.

[Formula 1]

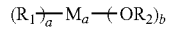

In Formula 1, $M_a$ is a Group IV or Group XIV element, for example, titanium (Ti), tin (Sn), or zirconium (Zr). $R_1$ is a $C_1$ to $C_{12}$, for example, $C_1$ to $C_{10}$, hydrocarbon group, specifically methyl, ethyl, propyl (or an isomer thereof), butyl (or an isomer thereof), pentyl (or an isomer thereof), hexyl (or an isomer thereof), heptyl (or an isomer thereof), octyl (or an isomer thereof), nonyl (or an isomer thereof), butenyl (or an isomer thereof), pentenyl (or an isomer thereof), cyclobutyl, cyclopentyl, cyclohexyl, cyclopentadienyl, cyclohexenyl, benzyl, phenylethyl, phenyl, tolyl, naphthyl, and the like. $R_2$ is a $C_1$ to $C_{12}$, for example, $C_3$ to $C_{10}$, linear or branched aliphatic hydrocarbon group or a $C_5$ to $C_{12}$, for example, $C_5$ to $C_{10}$, cyclic aliphatic hydrocarbon group, specifically methyl, ethyl, propyl (or an isomer thereof), butyl (or an isomer thereof), pentyl (or an isomer thereof), hexyl (or an isomer thereof), heptyl (or an isomer thereof), octyl (or an isomer thereof), nonyl (or an isomer thereof), butenyl (or an isomer thereof), pentenyl (or an isomer thereof), cyclobutyl, cyclopentyl, cyclohexyl, cyclopentadienyl, cyclohexenyl, and the like. In addition, a is an integer from 0 to 2; b is an integer from 2 to 4; and a+b is 4.

[Formula 2]

In Formula 2, $M_b$ and $M_c$ are each independently a Group IV or Group XIV element, for example, titanium (Ti), tin (Sn), or zirconium (Zr). $R_3$ and $R_5$ are each independently a $C_1$ to $C_{12}$, for example, $C_3$ to $C_{10}$, hydrocarbon group, for example, methyl, ethyl, propyl (or an isomer thereof), butyl (or an isomer thereof), pentyl (or an isomer thereof), hexyl (or an isomer thereof), heptyl (or an isomer thereof), octyl (or an isomer thereof), nonyl (or an isomer thereof), butenyl (or an isomer thereof), pentenyl (or an isomer thereof), cyclobutyl, cyclopentyl, cyclohexyl, cyclopentadienyl, cyclohexenyl, benzyl, phenylethyl, phenyl, tolyl, naphthyl, and the like. $R_4$ and $R_6$ are each independently a $C_1$ to $C_{12}$, for example, $C_3$ to $C_{10}$, linear or branched aliphatic hydrocarbon group or a $C_5$ to $C_{12}$, for example, $C_5$ to $C_{10}$, cyclic aliphatic hydrocarbon group, for example, methyl, ethyl, propyl (or an isomer thereof), butyl (or an isomer thereof), pentyl (or an isomer thereof), hexyl (or an isomer thereof), heptyl (or an isomer thereof), octyl (or an isomer thereof), nonyl (or an isomer thereof), butenyl (or an isomer thereof), pentenyl (or an isomer thereof), cyclobutyl, cyclopentyl, cyclohexyl, cyclopentadienyl, cyclohexenyl, and the like. In addition, c and e are each independently an integer from 0 to 2; d and f are each independently an integer from 1 to 3; and c+d and e+f are each independently 3.

Examples of the organometallic compound may include tetra-n-butoxy titanium, dibutyltin butoxide, and tetra-n-butoxy zirconium, without being limited thereto. These compounds may be used alone or as a mixture thereof.

In step (A) of the method for preparing an aromatic carbonate, a reaction mixture containing an aliphatic carbonate is prepared by reacting the organometallic compound with carbon dioxide. It is understood that step (A) is performed according to Reaction Formula 1. Such a process of preparing an aliphatic carbonate can be easily performed by those skilled in the art.

[Reaction Formula 1]

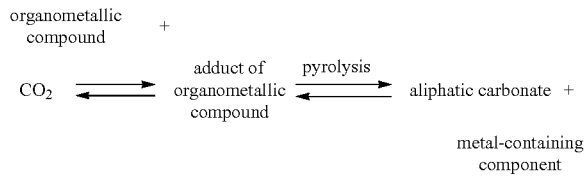

As can be seen from Reaction Formula 1, the reaction mixture contains a pyrolysate (a metal-containing component) which is formed simultaneously with an aliphatic carbonate upon pyrolysis of a carbon dioxide ($CO_2$) adduct of the organometallic compound. Such a metal-containing component originates from the organometallic compound and may include a hydrolysate of the organometallic compound or a hydrolysate of the carbon dioxide adduct of the organometallic compound, although difficult to specify in terms of structure. In addition, when the organometallic compound represented by Formula 1 is used, the metal-containing component may include hydrolysates of the organometallic compound represented by Formula 2 or a carbon dioxide adduct thereof, $(R_1)_a M_a=O$, and the like. When the organometallic compound represented by Formula 2 is used, the metal-containing component may include hydrolysates of $[(R_3)_c(OR_4)_d M_b$-O-$(R_5)_c(OR_6)_{f-1} M_c$-O$]_2$ or a carbon dioxide adduct thereof, and the like.

In one embodiment, preparing an aliphatic carbonate (step (A)) may be performed by typical batch reaction and may be performed at about 130° C. to about 230° C., for example, about 130° C. to about 200° C. at a carbon dioxide pressure of about 10 bar to about 200 bar, for example, about 10 bar to about 150 bar, for example, for about 0.5 to about 3 hours. Within this range, it is possible to secure rapid reaction and to prepare an aliphatic carbonate in high yield.

In addition, although preparing an aliphatic carbonate (step (A)) may be performed in different ways depending upon the used organometallic compound, step A may be performed in the presence of an alcohol containing a $C_1$ to $C_{12}$, for example, $C_3$ to $C_{10}$, linear or branched aliphatic hydrocarbon group or an alcohol containing a $C_5$ to $C_{12}$, for example, $C_5$ to $C_{10}$, cyclic aliphatic hydrocarbon group in order to prepare an aliphatic carbonate in higher yield. Here, an additive capable of improving reactivity may also be used.

When an alcohol is used in step (A), the alcohol preferably contains an aliphatic hydrocarbon group identical to a hydrocarbon group of an aliphatic carbonate to be prepared, and may include, for example, methanol, ethanol, propanol (or an isomer thereof), butanol (or an isomer thereof), pentanol (or an isomer thereof), hexanol (or an isomer thereof), heptanol (or an isomer thereof), octanol (or an isomer thereof), nonanol (or an isomer thereof), butenol (or an isomer thereof), pentenol (or an isomer thereof), cyclobutanol, cyclopentanol, cyclohexanol, cyclopentadienol, and cyclohexenol, without being limited thereto. When the alcohol is used, a weight ratio of the organometallic compound to the alcohol may range from about 1:1 to about 1:20, for example, about 1:1 to about 1:10. Within this range, it is possible to obtain an aliphatic carbonate in high yield.

In step (B) of the method for preparing an aromatic carbonate, an aromatic carbonate is prepared by reacting the reaction mixture with an aromatic alcohol. Specifically, in step (B), reaction (transesterification) of an aliphatic carbonate including the aliphatic carbonate in the reaction mixture with an aromatic alcohol is performed in the presence of the metal-containing component in the reaction mixture, as a transesterification catalyst. In the present invention, the aromatic carbonate may include an alkylaryl carbonate, a diaryl carbonate, or a mixture thereof.

The aromatic alcohol (aromatic hydroxy compound) may include an alcohol containing a $C_6$ to $C_{30}$ aromatic hydrocarbon group without limitation, and may include, for example, phenol, cresol (or an isomer thereof), xylenol (or an isomer thereof), trimethylphenol (or an isomer thereof), tetramethylphenol (or an isomer thereof), ethylphenol (or an isomer thereof), propylphenol (or an isomer thereof), butylphenol (or an isomer thereof), diethylphenol (or an isomer thereof), methylethylphenol (or an isomer thereof), methylpropylphenol (or an isomer thereof), dipropylphenol (or an isomer thereof), methylbutylphenol (or an isomer thereof), pentylphenol (or an isomer thereof), hexylphenol (or an isomer thereof), cyclohexylphenol (or an isomer thereof), methoxyphenol (or an isomer thereof), ethoxyphenol (or an isomer thereof), naphthol (or an isomer thereof), various substituted naphthols, hydroxypyridine (or an isomer thereof), hydroxycoumarine (or an isomer thereof), and hydroxyquinoline (or an isomer thereof), without being limited thereto. For example, the aromatic alcohol may include an alcohol containing a $C_6$ to $C_{10}$ aromatic group, specifically phenol. An aromatic group of the prepared aromatic carbonate varies depending upon the used aromatic alcohol. For example, when phenol is used, it is possible to prepare diphenyl carbonate.

In step (B), a weight ratio of a metal in the metal-containing component (organometallic compound) to the aromatic alcohol may range from about 1:25 to about 1:7,500, for example, about 1:50 to about 1:1,500. Within this range, it is possible to obtain an aromatic carbonate in high yield.

The aliphatic carbonate contains an aliphatic carbonate in the reaction mixture prepared in step (A), and may further include a separate aliphatic carbonate depending upon the amount of the used metal-containing component (organometallic compound). In other words, the aliphatic carbonate in the reaction mixture is reacted with the aromatic alcohol without being separated. In addition, the separate aliphatic carbonate may include an aliphatic carbonate having the same structure as the aliphatic carbonate in the reaction mixture, without being limited thereto.

In step (B), a weight ratio of the metal in the metal-containing component (organometallic compound) to the entire aliphatic carbonate used may range from about 1:25 to about 1:7,500, for example, about 1:50 to about 1:1,500. Within this range, it is possible to obtain an aromatic carbonate in high yield.

Further, a weight ratio of the aliphatic carbonate to the aromatic alcohol may range from about 1:0.5 to about 1:5, for example, about 1:0.5 to about 1:3. Within this range, it is possible to obtain an aromatic carbonate in high yield.

In addition, the metal in the metal-containing component may be present in an amount of about 50 ppm to about 15,000 ppm, for example, about 100 ppm to about 10,000 ppm in the entire reaction solution including the aliphatic carbonate, the aromatic alcohol, and the metal-containing component. Within this range, it is possible to obtain an aromatic carbonate in high yield.

In one embodiment, preparing an aromatic carbonate (step (B)) may be performed at about 100° C. to about 250° C., for example, at about 200° C. to about 250° C. at about 1 bar to about 30 bar, for example, at about 1 bar to about 10 bar, for example, for about 0.1 to 2 hours. Within this range, it is possible to secure rapid reaction and to prepare an aliphatic carbonate in high yield.

When the aromatic carbonate includes alkylaryl carbonate, the method may further include (C) producing diaryl carbonate and dialkyl carbonate, as by-products, by disproportionation of the alkylaryl carbonate. Such disproportionation can be easily performed by those skilled in the art.

In one embodiment, the disproportionation (step (C)) may be performed in succession to step (B) or in a batch manner, without being limited thereto. The disproportionation is preferably performed while extracting diaryl carbonate or dialkyl carbonate from the system.

The disproportionation may be performed in the presence of a catalyst, and, as the catalyst, the catalyst used in step (B) or a typical disproportionation catalyst may be used. When the catalyst is used, the catalyst may be present in an amount of about 0.0001 parts by weight to about 50 parts by weight based on 100 parts by weight of the alkylaryl carbonate, although the amount of the catalyst may vary depending upon the kind thereof, the kind and amount of the alkylaryl carbonate, reaction conditions such as reaction temperature and pressure, and the like.

Although the disproportionation may be performed under different conditions depending upon the kind of the used alkylaryl carbonate (base material), the disproportionation may be performed at a reactor temperature of about 50° C. to about 350° C., for example, about 100° C. to about 280° C. for about 0.001 to about 50 hours, for example, about 0.01 to about 10 hours. Although reaction pressure may vary depending upon the kind of the used base material, reaction temperature, and the like, the disproportionation may be generally performed at about 10 Pa to about 20 MPa. After completion of the disproportionation, the catalyst, the alkylaryl carbonate, the dialkyl carbonate, and the aromatic alcohol may be removed by a method known in the art, thereby obtaining diaryl carbonate.

As described above, the method for preparing an aromatic carbonate according to the present invention can economically prepare an aromatic carbonate through a simple process without a need for a separate separation process and an additional transesterification catalyst unlike a typical preparation method in the art. In addition, the preparation method according to the present invention can prepare an aliphatic carbonate in high yield through addition of an aliphatic alcohol in preparation of the aliphatic carbonate.

MODE FOR INVENTION

Hereinafter, the present invention will be described in more detail with reference to some examples. However, it should be understood that these examples are provided for illustration only and are not to be construed in any way as limiting the present invention.

EXAMPLE

Example 1

With tetra-n-butoxy titanium (10.1 g, 29.5 mmol) placed in a 75 ml autoclave reactor provided with an external heater, the reactor was heated to 180° C. while stirring, and carbon dioxide was introduced to a pressure of 120 bar, followed by reaction at 180° C. at 120 bar for 1 hour and cooling to room temperature. Thereafter, carbon dioxide was vented to return the reactor to atmospheric pressure, followed by analyzing a reaction mixture through gas chromatography. It was confirmed that di-n-butyl carbonate (aliphatic carbonate) was obtained in a yield of 39.5% (amount of di-n-butyl carbonate in the reaction mixture: 19.2% by weight (wt %)). In addition, it was confirmed that the amount of titanium in the reaction mixture was 13.4 wt % through inductively coupled plasma-optical emission spectrometry (ICP-OES) (step (A)).

Next, in a 12.3 ml tube reactor, phenol (4.1 g, 43.1 mmol), di-n-butyl carbonate (3.739 g, 21.5 mmol), and 0.0586 g of the reaction mixture obtained in the step (A) (containing 19.2 wt % of di-n-butyl carbonate and 13.4 wt % of titanium) were placed such that titanium was present in an amount of 1,000 ppm in the reaction solution, followed by closing the reactor. The reactor was placed in an oil stirred tank at 230° C. and maintained for 15 minutes and then transferred to a low temperature bath at −10° C., followed by quenching, thereby preparing butylphenyl carbonate (aromatic carbonate) (step (B)). A conversion rate of the aliphatic carbonate and selectivity of the aromatic carbonate were found through gas chromatography. Results are shown in Table 1.

Example 2

A reaction mixture (reaction solution) containing di-n-butyl carbonate (aliphatic carbonate) was prepared in the same manner as in step (A) of Example 1 except that, in step (A), n-butanol (24.4 g, 329.5 mmol) was further added and then removed through distillation after completion of reaction (yield of di-n-butyl carbonate: 98.0%, amount of di-n-butyl carbonate in the reaction mixture: 44.5 wt %, amount of titanium in the reaction mixture: 14.1 wt %).

Next, in a 12.3 ml tube reactor, phenol (4.1 g, 43.1 mmol), di-n-butyl carbonate (3.8 g, 21.5 mmol), and 0.0559 g of the reaction mixture obtained in the step (A) (containing 44.5 wt % of di-n-butyl carbonate and 14.1 wt % of titanium) were placed such that titanium was present in an amount of 1,000 ppm in the reaction solution, followed by closing the reactor. The reactor was placed in an oil stirred tank at 230° C. and maintained for 15 minutes and then transferred to a low temperature bath at −10° C., followed by quenching, thereby preparing butylphenyl carbonate (aromatic carbonate) (step (B)). A conversion rate of the aliphatic carbonate and selectivity of the aromatic carbonate were found through gas chromatography. Results are shown in Table 1.

Example 3

With dibutyltin dibutoxide (10.1 g, 26.6 mmol) placed in a 75 ml autoclave reactor provided with an external heater, the reactor was heated to 180° C. while stirring, and carbon dioxide was introduced to a pressure of 120 bar, followed by reaction at 180° C. at 120 bar for 1 hour and cooling to room temperature. Thereafter, carbon dioxide was vented to return the reactor to atmospheric pressure, followed by analyzing a reaction mixture through gas chromatography. It was confirmed that di-n-butyl carbonate (aliphatic carbonate) was obtained in a yield of 55.2% (amount of di-n-butyl carbonate in the reaction mixture: 22.62 wt %). In addition, it was confirmed that an amount of tin in the reaction mixture was 27.9 wt % through ICP-OES (step (A)).

Next, in a 12.3 ml tube reactor, phenol (4.1 g, 43.1 mmol), di-n-butyl carbonate (3.744 g, 21.5 mmol), and 0.0280 g of the reaction mixture obtained in step (A) (containing 22.6 wt % of di-n-butyl carbonate and 27.9 wt % of tin) were placed such that tin was present in an amount of 1,000 ppm in the reaction solution, followed by closing the reactor. The reactor was placed in an oil stirred tank at 230° C. and maintained for 15 minutes and then transferred to a low temperature bath at −10° C., followed by quenching, thereby preparing butylphenyl carbonate (aromatic carbonate) (step (B)). A conversion rate of the aliphatic carbonate and selectivity of the aromatic carbonate were found through gas chromatography. Results are shown in Table 1.

Example 4

A reaction mixture containing di-n-butyl carbonate was prepared in the same manner as in step (A) of Example 1 except that, in step (A), n-butanol (24.4 g, 329.5 mmol) was further added and then removed through distillation after completion of reaction (yield of di-n-butyl carbonate: 69.2%, amount of di-n-butyl carbonate in the reaction mixture: 29.4 wt %, amount of tin in the reaction mixture: 37.8 wt %).

Next, in a 12.3 ml tube reactor, phenol (4.1 g, 43.1 mmol), di-n-butyl carbonate (3.8 g, 21.5 mmol), and 0.0207 g of the reaction mixture obtained in step (A) (containing 29.4 wt % of di-n-butyl carbonate and 37.8 wt % of tin) were placed such that tin was present in an amount of 1,000 ppm in the reaction solution, followed by closing the reactor. The reactor was placed in an oil stirred tank at 230° C. and maintained for 15 minutes and then transferred to a low temperature bath at −10° C., followed by quenching, thereby preparing butylphenyl carbonate (aromatic carbonate) (step (B)). A conversion rate of the aliphatic carbonate and selectivity of the aromatic carbonate were found through gas chromatography. Results are shown in Table 1.

Comparative Example 1

In a 12.3 ml tube reactor, di-n-butyl carbonate (3.751 g, 21.5 mmol) and PbO (0.0084 g, 0.0377 mmol) as a catalyst were placed such that lead was present in an amount of 1,000 ppm in the reaction solution, followed by closing the reactor. The reactor was placed in an oil stirred tank at 230° C. and maintained for 15 minutes and then transferred to a low temperature bath at −10° C., followed by quenching, thereby preparing butylphenyl carbonate (aromatic carbonate) (step (B)). A conversion rate of the aliphatic carbonate and selectivity of the aromatic carbonate were found through gas chromatography. Results are shown in Table 1.

Property Evaluation

* Evaluation of yield, conversion rate, and selectivity: After performing each of the steps (steps (A) and (B)), the reaction solution was analyzed through gas chromatography (GC), followed by calculation of a yield of the aliphatic carbonate prepared in step (A) and a conversion rate of the aliphatic carbonate and selectivity of the aromatic carbonate in step (B) according to Equations 1 to 3. Here, the presence and weight of the aliphatic carbonate and the aromatic carbonate in the reaction solution can be confirmed through GC, and mole number can be found by dividing weight by molecular weight.

Yield of aliphatic carbonate (%)=(Mole number of produced aliphatic carbonate/Mole number of added organometallic compound)×100    [Equation 1]

Conversion rate of aliphatic carbonate (%)=(Mole number of consumed aliphatic carbonate/Mole number of introduced aliphatic carbonate)×100    [Equation 2]

Selectivity of aromatic carbonate (%)=(Mole number of produced aromatic carbonate/Mole number of consumed aliphatic carbonate)×100    [Equation 3]

TABLE 1

|  | Organometallic compound | Step (A) Yield of aliphatic carbonate (%) | Step (B) Conversion rate of aliphatic carbonate (%) | Step (B) Selectivity of aromatic carbonate (%) |
| --- | --- | --- | --- | --- |
| Example 1 | Ti(OBu)$_4$ | 39.5 | 8.4 | 99.7 |
| Example 2 | Ti(OBu)$_4$ | 98.0 | 8.5 | 99.8 |
| Example 3 | Bu$_2$Sn(OBu)$_2$ | 55.2 | 7.2 | 99.8 |
| Example 4 | Bu$_2$Sn(OBu)$_2$ | 69.2 | 7.1 | 99.7 |
| Comparative Example 1 | PbO (catalyst) | — | 6.8 | 99.5 |

From the results shown in Table 1, it can be seen that the method for preparing an aromatic carbonate according to the present invention can economically prepare an aromatic carbonate through a simple process without a need for a separate separation process and an additional transesterification catalyst such as PbO used in Comparative Example 1.

In addition, the method according to the present invention can prepare an aliphatic carbonate in higher yield through addition of an aliphatic alcohol in preparation of an aliphatic carbonate.

It should be understood that various modifications, changes, alterations, and equivalent embodiments can be made by those skilled in the art without departing from the spirit and scope of the invention.

The invention claimed is:

1. A method for preparing an aromatic carbonate, comprising:
    (A) preparing a reaction mixture containing an aliphatic carbonate by reacting an organometallic compound with carbon dioxide; and
    (B) preparing an aromatic carbonate by reacting the reaction mixture with an aromatic alcohol,
    wherein the organometallic compound comprises at least one of an organometallic compound represented by Formula 1 and an organometallic compound represented by Formula 2:

[Formula 1]

wherein $M_a$ is a Group IV or Group XIV element; $R_1$ is a $C_1$ to $C_{12}$ hydrocarbon group; $R_2$ is a linear or branched $C_1$ to $C_{12}$ aliphatic hydrocarbon group or a cyclic $C_5$ to $C_{12}$ aliphatic hydrocarbon group; a is an integer from 0 to 2; b is an integer from 2 to 4; and a+b is 4,

[Formula 2]

wherein $M_b$ and $M_c$ are each independently a Group IV or Group XIV element; $R_3$ and $R_5$ are each independently a $C_1$ to $C_{12}$ hydrocarbon group; $R_4$ and $R_6$ are each independently a linear or branched $C_1$ to $C_{12}$ aliphatic hydrocarbon group or a cyclic $C_5$ to $C_{12}$ aliphatic hydrocarbon group; c and e are each independently an integer from 0 to 2; d and f are each independently an integer from 1 to 3; and c+d and e+f are each independently 3.

2. The method according to claim 1, wherein the aliphatic carbonate in the reaction mixture is reacted with the aromatic alcohol without being separated.

3. The method according to claim 1, wherein the organometallic compound contains a metal-oxygen-carbon bond.

4. The method according to claim 1, wherein preparing an aliphatic carbonate (step (A)) is performed at about 130° C. to about 230° C. at a carbon dioxide pressure of about 10 bar to about 200 bar.

5. The method according to claim 1, wherein preparing an aromatic carbonate (step (B)) is performed at about 100° C. to about 250° C. at about 1 bar to about 30 bar.

6. The method according to claim 1, wherein preparing an aliphatic carbonate (step (A)) is performed in the presence of an alcohol containing a linear or branched $C_1$ to $C_{12}$ aliphatic hydrocarbon group or an alcohol containing a cyclic $C_5$ to $C_{12}$ aliphatic hydrocarbon group.

\* \* \* \* \*

UNITED STATES PATENT AND TRADEMARK OFFICE
CERTIFICATE OF CORRECTION

| | | |
|---|---|---|
| PATENT NO. | : 9,765,013 B2 | |
| APPLICATION NO. | : 15/025379 | |
| DATED | : September 19, 2017 | |
| INVENTOR(S) | : Chang Hoon Lee et al. | |

It is certified that error appears in the above-identified patent and that said Letters Patent is hereby corrected as shown below:

In the Specification

Column 5, delete Line 8 and insert: --hydrolysates of $[(R_3)_c(OR_4)_dM_b\text{-}O\text{-}(R_5)_e(OR_6)_{f\text{-}1}M_c\text{-}O]_2$--

Signed and Sealed this
Seventeenth Day of April, 2018

Andrei Iancu
*Director of the United States Patent and Trademark Office*